(12) United States Patent
Bauer

(10) Patent No.: US 6,342,347 B1
(45) Date of Patent: *Jan. 29, 2002

(54) ELECTROMAGNETIC SENSOR

(75) Inventor: Alan Joseph Bauer, Jerusalem (IL)

(73) Assignee: Biosensor Systems Design., Inc., Cedarhurst, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/426,564

(22) Filed: Oct. 22, 1999

(51) Int. Cl.$^7$ .............................. C12Q 1/00; C12M 1/34; C12M 1/00
(52) U.S. Cl. ...................... 435/4; 435/287.1; 435/289.1; 435/283.1; 204/403; 204/164
(58) Field of Search ...................... 435/4, 287.1, 289.1, 435/283.1; 204/403, 164

(56) References Cited

U.S. PATENT DOCUMENTS

| | | | |
|---|---|---|---|
| 4,822,566 A | 4/1989 | Newman | 422/68 |
| 4,916,075 A | 4/1990 | Malmros et al. | 435/291 |
| 5,156,810 A | 10/1992 | Ribi et al. | 422/82.01 |
| 5,264,103 A | 11/1993 | Yoshioka et al. | 204/403 |
| 5,389,215 A * | 2/1995 | Hirouchi et al. | 204/403 |
| 5,491,097 A | 2/1996 | Ribi et al. | 436/518 |
| 5,543,326 A | 8/1996 | Heller et al. | 436/817 |
| 5,585,646 A | 12/1996 | Kossovsky et al. | 257/40 |
| 5,605,662 A | 2/1997 | Heller et al. | 422/68.1 |
| 5,620,854 A | 4/1997 | Holzrichter et al. | 435/6 |
| 5,719,033 A | 2/1998 | Ackley et al. | 435/7.92 |
| 5,783,056 A | 7/1998 | Hampp et al. | 204/403 |
| 6,096,497 A * | 8/2000 | Bauer | 435/4 |

FOREIGN PATENT DOCUMENTS

| | | |
|---|---|---|
| EP | 0 441 120 | 8/1991 |
| WO | WO 97/01092 | 1/1997 |
| WO | WO 97/22875 | 6/1997 |
| WO | WO 97/41425 | 11/1997 |

OTHER PUBLICATIONS

Radmacher, Manfred et al. Direct Observation of Enzyme Activity with the Atomic Force Microscope. Science 265:1577, Sep. 9, 1994.

Patel et al., Immobilization of Protein Molecules onto Homogeneous and Mixed Carboxylate–Terminated Self–Assembled Monolayers. Langmuir 6485–6490, 1997.

Bardea, Amos et al., NAD+ Dependent Enzyme Electrodes: Electrical Contact Cofactor–Dependent Enzymes and Electrodes. J. Am. Chem Soc. 119:9114–91119, 1997.

Willner, Itamar et al., Assembly of Functionalized Monolayers of Redox Proteins on Electrode Surfaces: Novel Bioelectronic and Optobioelectronic Systems. Biosensors & Bioelectronics 12, No. 4, pp. 337–356, 1997.

Wilner et al. NAD$^{30}$–Dependent Enzyme Electrodes: Electrical Contact of Cofactor–Dependent Enzymes and Electrodes, J. Am. Chem. Soc., 1997, 9114–9119.

Souteyrand, E. et a., Direct Detection of Biomolecules by Electrochemical Impedance Measurements, Sensors and Actuators B, vol. 20, No. 1, pp. 63–69, May 1, 1994.

* cited by examiner

*Primary Examiner*—Louise N. Leary
(74) *Attorney, Agent, or Firm*—Arthur S. Bickel

(57) ABSTRACT

The present invention relates to a sensor for analyte detection. The sensor makes use of changes in electrostatic fields associated with macromolecular binding agents during their interaction with analytes. Specifically, analyte presence leads to increases in magnetic flux generated by the motions of the binding agent electrostatic material. Magnetic or induced electrical signals may be monitored for change in order to detect analyte in a sample of interest.

20 Claims, 6 Drawing Sheets

ELECTROMAGNETIC SENSOR

BACKGROUND OF THE INVENTION

1. Field of the Invention

This invention pertains to the detection of analyte through the monitoring of induced electron motion in conducting elements. The present invention is an improvement of the inventions disclosed in pending U.S. patent application Ser. No. 09/110,686, now U.S. Pat. No. 6,096,497, which is herein incorporated by reference, and PCT application PCT/IL99/00309. The present invention describes in greater detail a method and device for detecting induced base member electron motions responsive to analyte presence.

2. Description of the Related Art

In the aforementioned patent applications, a sensor for analyte detection is described. The sensor is very sensitive, quick in response, easy to prepare, rugged, and inexpensive to produce. Yet, the specific interaction of the sensor strip contact region and detector electrodes was never fully explored. In this application, this aspect of the sensor described previously will be addressed.

SUMMARY OF THE INVENTION

It is therefore a primary object of the present invention to provide an improved electrical contact between detection unit electrodes and sensor strip in a sensor system that utilizes a method of detection, in which the fluctuations of macromolecular-associated electrostatic fields in proximity to an electrically-conducting base member induce de novo electron motion in the base member; and It is a further object of the invention to describe an optimal sensor strip-embodiment for electrode contact to allow for rapid detection of analyte.

It is an additional object of the invention to improve the consistency of detection of an analyte in a sensor system.

These and other objects of the present invention are attained by a sensor which has one or a plurality of electrically conductive or semiconductive base members, and at least one macromolecular entity disposed proximate each base member and interactive at a level of specificity with at least one predetermined analyte. Electron motion induced in the conducting portion of the base member is responsive to the interaction of the macromolecular entity with analyte. A detection unit detects the induced electron motion through contact or proximity of associated electrical leads to the base member and/or a conductive or semiconductive layer proximate each base member.

Optionally a self-assembled monolayer (SAM) or other chemical entity is bound to each base member, proximate the macromolecular entity. Macromolecular entities are arranged in a monolayer or multilayer.

According to an aspect of the invention a plurality of macromolecular entities is employed for the detection of at least one analyte.

According to another aspect of the invention electrical leads of the detection unit are coupled to the base member and/or a proximate conductive or semiconductive layer proximate at no more than two positions. The coupling may be passive. The induced electrical signal measured by a detection unit attached to these electrodes, or a component of said signal, may be processed for analyte detection or quantification.

According to yet another aspect of the invention each base member is a conducting foil, coating, thin-film, ink, or solid piece.

According to an additional aspect of the invention, the proximate conductive or semiconductive layer is prepared from organic or inorganic semiconductors In a further aspect of the invention a packaging layer is disposed above the macromolecular entity, the packaging layer being soluble in a medium that contains the analyte. Electrode contact to sensor strip may be made on the conductive layer formed from macromolecule and packaging layer on the base member.

The invention provides a method for detecting an analyte, having the following steps: providing one or a plurality of electrically conductive base members; immobilizing at least one macromolecule in proximity to at least one side of each base member, wherein the macromolecule is capable of interacting at a level of specificity with a predetermined analyte; depositing a conducting or semiconducting layer proximate the base member, this layer being optionally separated from the base member by other material; contacting leads of a detection unit to said base member and conducting or semiconducting layer; and, detecting induced electron motion in these layers, and signal is responsive to analyte presence.

Optionally a self-assembled monolayer or chemical entity is bound to each base member, the macromolecules are immobilized proximate to the self-assembled monolayer on at least one side of the base member.

According to another aspect of the invention, a plurality of macromolecules having different specificity of interaction with analyte are immobilized for the detection of at least one analyte.

Preferably the step of detecting is performed by coupling electrical leads of a detection unit to the base member and the conductive or semiconductive layer proximate each base member at no more than two positions per sensor strip. The coupling may be passive.

According to yet another aspect of the invention, the macromolecular entities are arranged in a monolayer or multilayer proximate the base member.

According to still another aspect of the invention, a packaging layer is disposed above the macromolecules, the packaging layer being soluble in a medium that contains the analyte. The packaging and macromolecular layers may serve as the conductive or semiconductive layer disposed proximate the base member.

According to an additional aspect of the invention, a further step comprises processing the induced electrical signal or a component thereof for determination of analyte presence or quantity.

BRIEF DESCRIPTION OF THE DRAWING

For a better understanding of these and other objectives of the present invention, reference is made to the following detailed description of the invention, by way of example, which is to be read in conjunction with the following drawings, wherein.

DESCRIPTION OF THE PREFERRED EMBODIMENT

Figure 6:
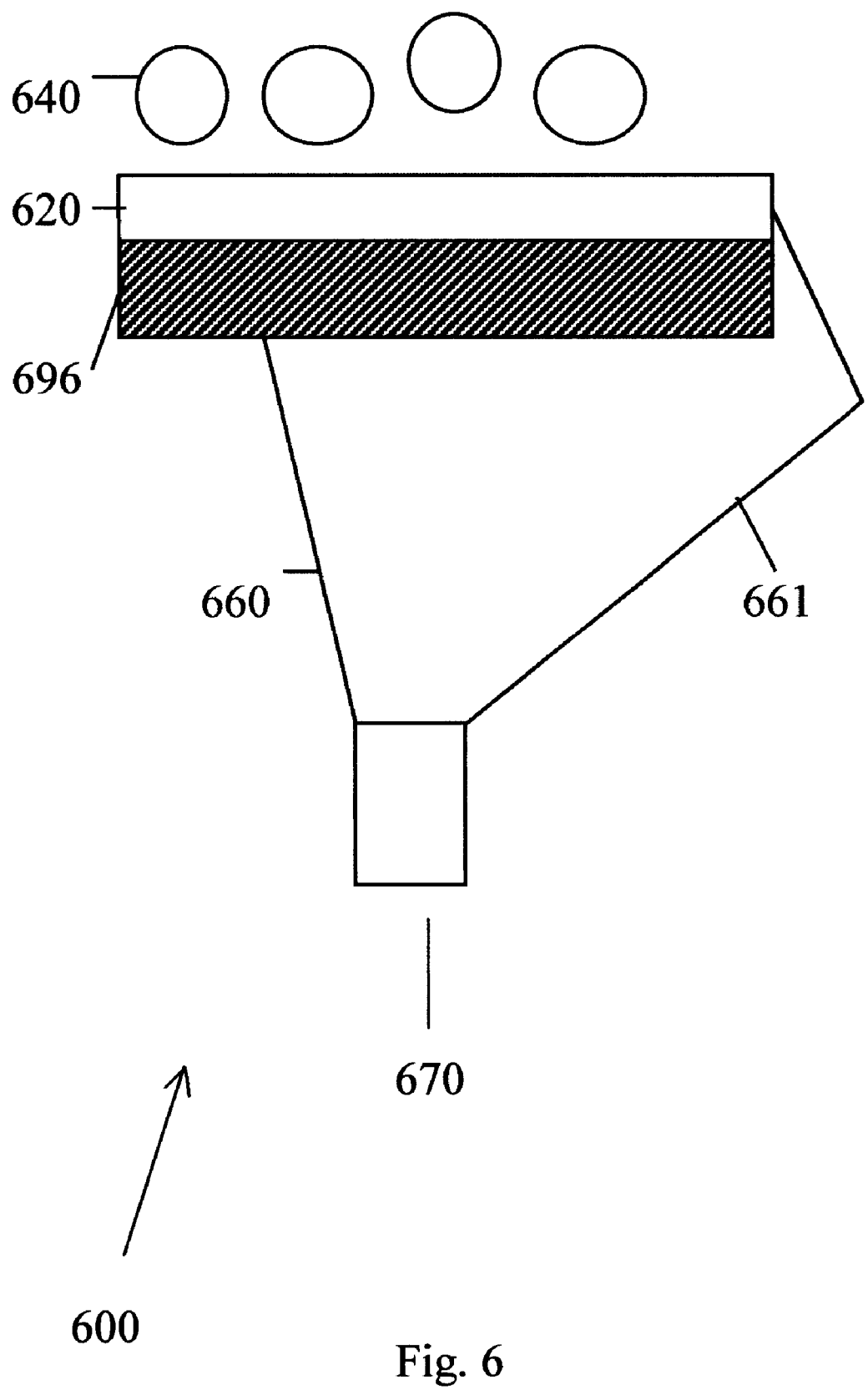
FIG. 6 is a schematic view of a fifth alternate embodiment of a sensor 600 in accordance with the invention in which electrical leads 660 and 661 of a detection unit (670) are passively contacted to a base member (620) and proximate semiconducting layer (696).

Without being bound by any particular theory, the following discussion is offered to facilitate understanding of the invention. The sensor design disclosed herein is based on electromagnetic induction of electrons in conducting materials when said electrons are exposed to fluctuating macromolecular electrostatic fields. The sensor utilizes a novel method of detecting an analyte wherein macromolecular binding agents are first immobilized proximate an electrically conductive base member. The bound macromolecules are always moving; the motions of the electrostatic fields associated with the macromolecules serve to induce electron motions in the base member. Base member electrons are caused to move by the process of electromagnetic induction. Signals such as induced current, magnetic field strength, induced electromotive force, changes in impedance or resistance, signal sign switching, signal frequency, electrical noise and components thereof can be monitored for change during exposure of the macromolecular binding agents to a sample that may contain target analyte. For example, the electrons moving between a base member 620 and an electrically-contacted proximate semiconducting layer 696 a move less rapidly in the semiconducting layer 696 (shown with hatching in FIG. 6) and thus allow for easy measurement of an induced electrical signal through passive contact of electrodes 660 and 661 with the conducting base member 620 and the proximate semiconducting layer 696. Alternatively, referring to FIG. 2, electrons moving in the base member 220 in response to macromolecule 240 interaction with analyte (not shown) can be detected through measurement of a voltage across the base member 220 and proximate conductive layer 295, when partially insulating material 290 is disposed therebetween. One can additionally process or analyze the induced signal-or a component thereof-by Fourier transform methods, band pass filtering, signal signature analysis, or other means. Such signal processing may be performed by the detection unit 270, or with an additional processing unit (not shown), for example a computer with appropriate software. Changes in the electrostatic fields of the macromolecules before and during interaction with analyte result from altered motional behavior of the charged/polar macromolecules themselves and/or the presence of additional electrostatic material associated with the analyte. Altered electrostatic fields (size) or changed macromolecule motions (rate of fluctuation) induce additional electron motion in the base member and altered induced electrical signals that can be measured between base member 220 and conductive layer 295 or across a hybrid conductive base member 620 and a semiconductive layer 696 as shown in FIG. 6.

A typical sensor comprises (i) a multilayer substrate comprising a conducting base member and an optional self-assembled monolayer (or other chemical entity that rests between the base member and the macromolecules); (ii) at least one macromolecule that displays a level of affinity of interaction toward a predetermined analyte or group of analytes; (iii) a conductive or semiconductive layer proximate the base member; and (iv) a detection unit for detecting magnetic or electrical signals caused by induced electron motions in the base member and responsive to the presence of analyte. Optionally, a unit for processing the induced signal or a component thereof may be included. Additionally, a computer may be used for controlling sample handling and monitoring the signal or processed signal.

According to a method of the invention, one first immobilizes one or more biological or synthetic macromolecules in proximity to an appropriately conductive base member and then measures an electromotive force (emf), current, or other electrical effect induced across the base member and a nearby, separate, conductive layer (see definitions below) as a result of analyte-related changes in fluctuating electrostatic fields associated with the macromolecular binding agents. The conductive layer may be separated from the conductive portion of the base member by other material. Metal oxides, biological materials, self-assembled monolayers, deposited chemical layers, and the like may be employed to define the level of electrical connectivity between the conductive layer and the base member. In the case of a semiconductive conductive layer, such additional separation may not be necessary. It is the motion of the electrons in the conductive base member in response to action of the macromolecules that are the cause of the measured electrical signals such as current and induced electromagnetic force across the base member and proximate conductive layer.

As described in the noted patent application PCT/IL99/00309, the methodology of detection is very sensitive. Detection of pathogenic bacteria in a complex meat matrix was performed within two minutes at 1–10 cells per milliliter of sample (concentration determined by plating). The method takes advantage of the presence of a conducting or semiconducting layer proximate the base member. Such a layer may be formed from macromolecules, self-assembled monolayers, deposited chemical layers, inorganic semiconductors, and the like. Proteins are known to act as semiconducting materials and may serve as conductive layer in some sensor systems embodiments. Induced motion of base member electrons in response to binding agent action generates large numbers of magnetic fields, and these magnetic fields generate measurable magnetic and electrical signals. Measurement of induced current or voltage in a sensor strip of base member and proximate conductive layer allows for rapid determination of analyte presence. Complete electrical isolation of the conducting portion of the base member from the proximate conductive layer may lead to loss of signal. Such difficulties can be avoided according to the invention disclosed herein.

In the following description, numerous specific details are set forth in order to provide a thorough understanding of the present invention. It will be apparent, however, to one skilled in the art that the present invention may be practiced without these specific details. In other instances well known circuits and control logic have not been shown in detail in order not to unnecessarily obscure the present invention.

Certain terms are now defined in order to facilitate better understanding of the present invention. An "analyte" is a material that is the subject of detection or quantification. A "base member" or base layer is a solid or liquid element on or near which macromolecules can be physically or chemically immobilized for the purpose of sensor construction.

"Macromolecules", "macromolecular binding agents", or "macromolecular entities" can be any natural, mutated, synthetic, or semi-synthetic molecules that are capable of interacting with a predetermined analyte or group of analytes at a level of specificity.

A "self-assembled monolayer" or "SAM" is herein defined as a class of chemicals that bind or interact spontaneously or otherwise with a metal, metal oxide, glass, quartz or modified polymer surface in order to form a chemisorbed monolayer. As the phrase "self-assembled" implies, a self-assembled monolayer is formed from molecules that bond with the surface upon their direct contact from solvent, vapor, or spray. As the word "monolayer" implies, a self-assembled monolayer possesses a molecular thickness, i.e., it is ideally no thicker than the length of the longest molecule used therein. In practice, this may not be the case, but a thicker chemical layer between macromolecules and base member is acceptable for sensor construction.

A "chemical entity" is a non-SAM layer disposed proximate the base member. It will generally serve to partially insulate the base member from a conductive layer that is disposed proximate the SAM or chemical entity. A chemical entity may be deposited on or near a base member by any means.

A "packaging layer" is defined as a chemical layer disposed above the macromolecules. The packaging layer may aid in long term stability of the macromolecules, and in the presence of a sample that may contain analyte of interest, the packaging layer may dissolve to allow for rapid interaction of analyte and binding agents. The packaging layer may also serve in conjunction with the charged macromolecules in the role of conductive layer. Such is the case when a sensor is coated equally on both sides with SAM's (or chemical entities), macromolecules, and packaging layers.

A "sensor strip" is defined as a minimum of a single base member and associated macromolecule or macromolecules. If SAM or packaging layer is present, it is included in the term sensor strip. Additionally, the conductive layer and any associated insulating material may additionally be included in the term "sensor strip" unless they are not physically associated with the base member-macromolecule sensor strip unit.

An "electrode" or "lead" is a wire, electrical lead, connection, or the like that is attached at one end to a detection unit and contacted at the other end directly or indirectly to the base member and/or conductive layer portion of the sensor strip. Contact is generally electrically passive in nature and occurs at two positions. Generally, one electrode contacts the base member, while the second contacts a proximate conductive layer, although both electrodes may be contacted directly to a semiconductive conductive layer. The electrodes may be prepared from either conducting or semiconducting materials or a combination thereof.

"Induced" and "induction" are used with respect to the electrical arts. Specifically by these terms it is intended to exclude oxidation-reduction chemistries and applied electrical signals. An "induced" signal is a signal that is produced de novo without any required application to the sensor strip of electrical or electromagnetic signal. Additionally, in an induced signal, there is no oxidative transfer of electrons between the base member and binding agent or analyte.

A "detection unit" is any device that allows for the detection of induced electron motions in a base member. The detection unit is generally contacted to the conductive layer and base member portions of a sensor strip at two positions through passive contact of electrodes. The detection unit may possibly measure an induced electrical signal, and it may further process the signal or a component thereof for the purpose of analyte detection and concentration range determination.

A "conductive layer" refers to a layer or entity that is proximate the base member and is conductive or semiconductive in nature. The conductive layer may be prepared from organic or inorganic substances, semiconductors, charged chemical or biological materials, deposited (by any means) conductors or semiconductors, or any material that is not insulating. The conductive layer may be physically associated with a sensor strip or with electrodes of a detection unit (and brought into proximity to the sensor strip). The conductive layer may be realized as a conductor applied to a semiconductor.

Figure 1:
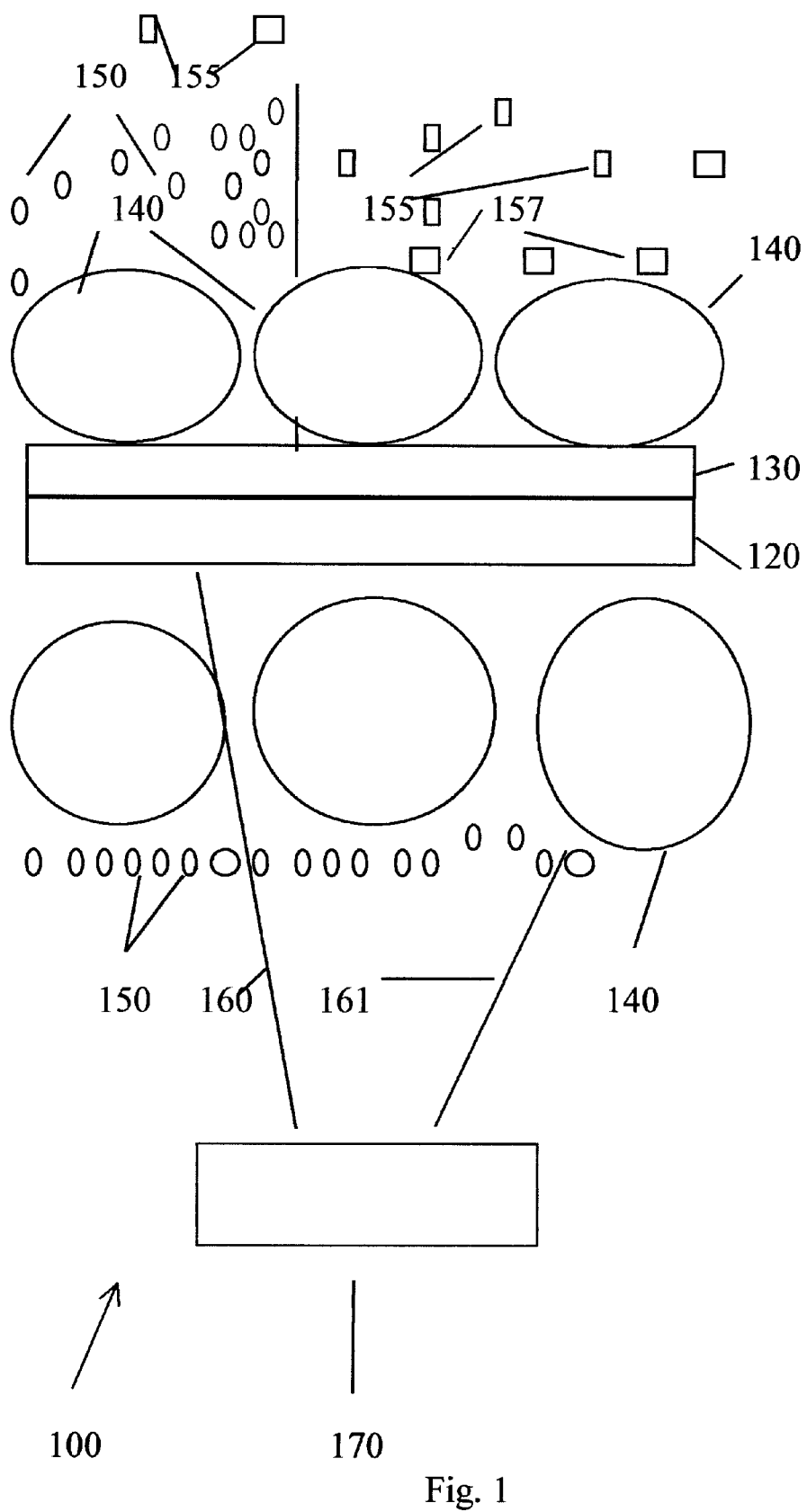
FIG. 1 is a schematic view of a sensor 100 in accordance with the invention in which a single base member 120 with macromolecule layer 140 and a packaging layer 150 is passively connected to the leads 160 and 161 of a detection unit 170. A self-assembled monolayer 130 is deposited between the base member and the macromolecules.

Referring now to FIG. 1, which schematically illustrates a preferred embodiment of the invention, free analyte 155 is disposed proximate a sensor 100 prior to (left side of figure) and after (right side of figure) dissolution of packaging layer 150. The analyte (shown as free analyte 155, and analyte 157 interacting with macromolecule layer 140) can be a member of any of the following categories, listed herein without limitation: cells, organic compounds, antibodies, antigens, virus particles, pathogenic bacteria, metals, metal complexes, ions, spores, yeasts, molds, cellular metabolites, enzyme inhibitors, receptor ligands, nerve agents, peptides, proteins, fatty acids, steroids, hormones, narcotic agents, synthetic molecules, medications, nucleic acid single-stranded or double-stranded polymers. The analyte 155 can be present in a solid, liquid, gas or aerosol. The analyte 155 could even be a group of different analytes, that is, a collection of distinct molecules, macromolecules, ions, organic compounds, viruses, spores, cells or the like that are the subject of detection or quantification. Some of the analyte 157 physically interacts with the sensor after dissolution of the packaging layer 150 and causes an increase in electromagnetically induced electron motion in the conductive portion of the base member 120. Contact of electrode 161 to the semiconductive macromolecule layer 140 and electrode 160 to base member 120 allows for measurement of de novo electrical signals that are responsive to the moving electrons in the base member 120. The semiconductive nature of proteins is very important for the measurement shown in FIG. 1. In observations of prototype sensors, one-sided coatings of penicillinase on aluminum foil did not lead to any readings, as one side had enzyme facing analyte, but no protein semiconductive region on the electrode contact side, while in opposite orientation, the analyte-facing side had no enzyme for analyte interaction, though there was protein available for contact with electrodes. When the penicillinase side was contacted to water containing ampicillin, and a silicon semiconductor was placed on the side that lacked enzyme, then a voltage was recorded through leads of a digital multimeter contacting the silicon semiconducting chip at two positions.

Examples of macromolecular entities suitable for use in the sensor 100 include but are not limited to enzymes that recognize substrates and inhibitors; antibodies that bind antigens, antigens that recognize target antibodies, receptors that bind ligands, ligands that bind receptors, nucleic acid single-strand polymers that can bind to form DNA-DNA, RNA-RNA, or DNA-RNA double strands, and synthetic molecules that interact with targeted analytes. The present invention can thus make use of enzymes, peptides, proteins, antibodies, antigens, catalytic antibodies, fatty acids, receptors, receptor ligands, nucleic acid strands, as well as synthetic macromolecules in the role of macromolecule layer 140. Natural, synthetic, semi-synthetic, over-expressed and genetically-altered macromolecules may be employed as binding agents. The macromolecule layer 140 may form monolayers as in FIG. 1, multilayers as in FIG. 2 , or mixed layers of several distinct binding agents (not shown). A monolayer of mixed binding agents may also be employed (not shown).

The macromolecule component is neither limited in type or number. Enzymes, peptides, receptors, receptor ligands, antibodies, catalytic antibodies, antigens, cells, fatty acids, synthetic molecules, and nucleic acids are possible macromolecular binding agents in the present invention. The sensor method may be applied to nearly any macromolecule because it relies on the following properties shared by substantially all macromolecular binding agents:

(1) that the macromolecules chosen as binding agents are highly specific entities designed to bind only with a selected analyte or group of analytes;

(2) that macromolecules have associated electrostatic fields due to charged and electrically-polar components of the macromolecules;

(3) that the electrostatic fields associated with the macromolecular binding agents fluctuate or change significantly in the presence of target analyte or analytes; such fluctuations can be caused by additional motions of the binding agent (enzymes) or by additional electrostatic material from the analyte that contributes to the electrostatic environment (non-enzyme binding agents); and (4) that the fluctuating electrostatic fields can induce an analyte-responsive electron motion in an electrically-conductive base member proximate to which the macromolecules are present.

For example, in the alternate embodiment of FIG. 6, an induced current may be measured in a closed electrical circuit that contains a base member 620 and a semiconductive layer 696 present proximate the base member and its associated macromolecules 640. A relatively small background induced current is present in the circuit due to fluctuations of the macromolecular electrostatic fields prior to sample contact. Presence of analyte in sample causes increased motions of electrons in the base member and thus a larger induced current as measured by a detection device 670 that is passively contacted through electrodes 660 and 661 to the base member 620 and semiconductive layer 696 . The resistance between the two electrodes may be in the mega-ohm range. Referring again to FIG. 1, while macromolecule layer 140 and packaging layer 150 may serve the role of a conductive layer, a deposited or solid conductive layer 295 (FIG. 2) is more effective in this role, as contact of the electrodes to the conductive layer is more consistent. The packaging layer 150 and macromolecule layer 140 (FIG. 1) are uneven in their surface properties, and excessive electrode pressure during fabrication or from an ad hoc application of the electrodes 160, 161 during a sensing operation can short out the circuit as a consequence of both electrodes 160, 161 being in a nonresistive mode of contact with base member 120 which can under certain conditions lead to a condition of no signal. A partially insulating layer 290 (FIG. 2) may serve to attenuate the effect of the moving base member electrons from the conductive layer 295 used in signal detection. If the conductive layer is semiconductive in nature, then such an insulating layer 290 may be unnecessary, as shown in the embodiment of FIG. 6. Since semiconductors have higher resistivities than conductors, the induced electrical signals can be more easily measured across the base member and conductive layer. Natural metal oxides, SAM's, chemically-deposited layers, and even macromolecules may serve to partially insulate the base member from the conductive layer, and thus lead to the generation of a relatively large induced emf or voltage between the two layers. The conductive layer may be any conducting or semiconducting material; organic and inorganic semiconductors are preferred.

The broad and generally applicable nature of the present invention is preserved during binding of macromolecules 240 in proximity to the base member 220 because binding can be effected by either specific covalent attachment or general physical absorption. It is to be emphasized that the change in monitored signal that is associated with analyte presence does not depend on any specific enzyme chemistries, optical effects, fluorescence, chemiluminescence, oxidation/reduction phenomena or applied electrical signals. This feature is an important advantage of the present invention. Additionally, according to the operation of the invention, current is actually generated, and the generated electricity may be of use in powering devices such as the sensor itself The macromolecules 240 rest within a distance from the base member 220 that allows for induction of base member electrons in response to fluctuations of macromolecular electrostatic fields A chemical entity or SAM may be disposed between the base member and the macromolecules. For the purposes of this invention, "proximate" with respect to macromolecule disposition relative the base member refers to any distance that allows for macromolecule-related induction of electrons in the base member, said electron induction being responsive to the presence of analyte.

Similarly, the disposition of the conductive layer 295 relative the base member 220 is such that an induced signal may be measured in or about an electrical circuit that includes base member and the optional conductive layer, and said signal is responsive to analyte presence. One may alternatively measure the magnetic fields generated in the base member 220 directly without recourse to the conductive layer that is used for easy measurement of an induced electrical signal. A layer 290 that partially isolates the conductive layer 295 from the conductive portion of the base member 220 may be disposed between the conductive layer 295 and the conducting portion of the base member 220. The relative disposition of the conductive layer 295 is such that the two layers are electrically-connected, even if there is partially insulating material between them. The system thus serves as a cascade: motion of electrostatic material associated with one or more binding elements causes large-scale electron motion in the base member; these latter electron motions spawn easily measurable induced electrical signals.

Figure 2:
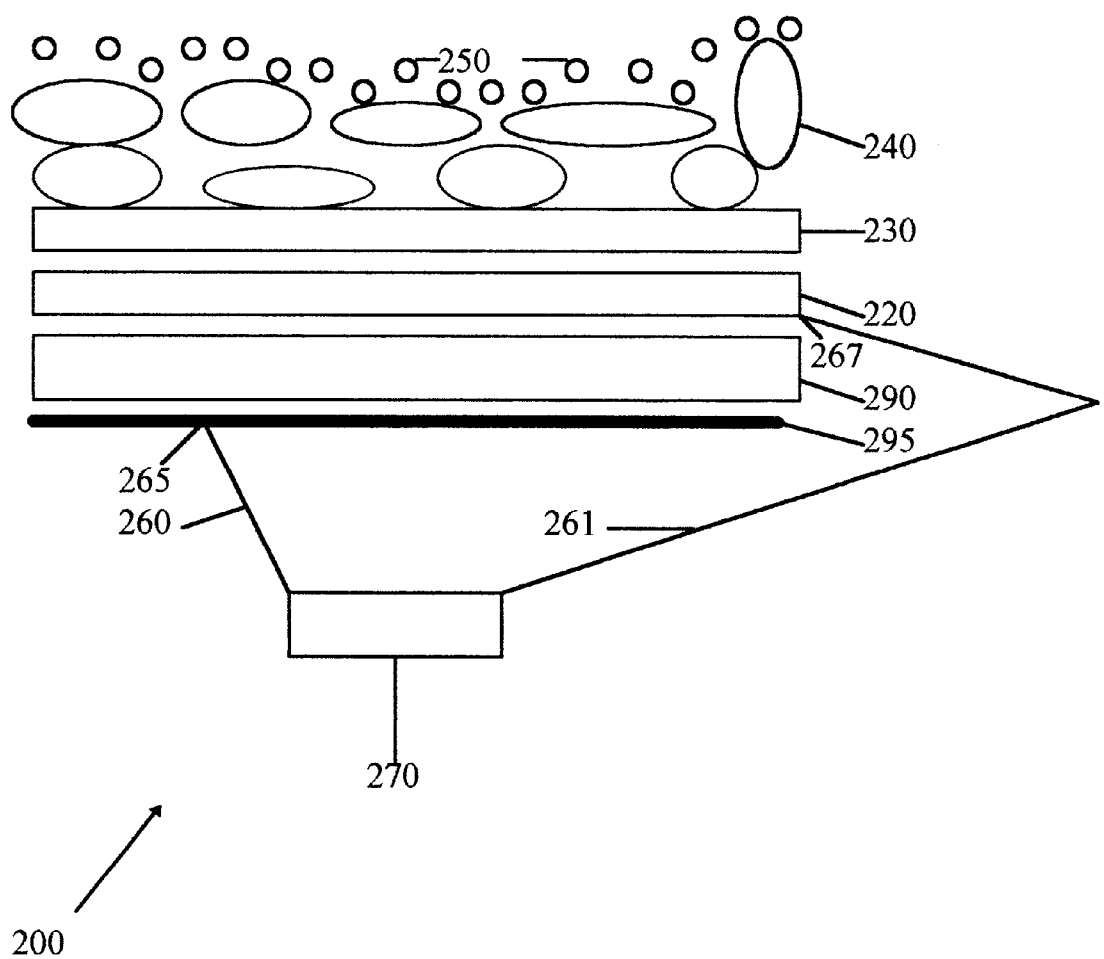
FIG. 2 is a schematic view of a first alternate embodiment of a sensor 200 in accordance with the invention in which a chemical layer 230 and macromolecules 240 are deposited on one side of a base member 220, while a partially electrically-insulating material 290 and conductive layer 295 are deposited on the opposite side. Electrodes 260 and 261 contact the sensor strip at positions 265 and 267 and lead to a detection unit 270.

Proximate with respect to conductive layer-base member separation refers to any distance that allows for measurement of an induced signal in the conductive layer or between the conductive layer and the base member, and said signal is responsive to analyte presence. As shown in FIG. 2, partial electrical insulation between the conducting layer 295 and conducting portions of the base member 220 may be accomplished by the presence of a natural metal oxide (such as aluminum oxide on aluminum foil) or the deposition of insulating material which forms the layer 290 between the base member 220 and the conducting layer 295.

The detection unit 270 is any device that can detect one or more signals resultant from analyte-responsive induced electron motions in the base member 220. Examples of such signals include but are not limited to induced current; magnetic fields strength; induced electromotive force; voltage; impedance; signal sign, frequency component or noise signature of a predetermined electrical signal propagated into a conductive layer at a first location and received at a second location. While a detection unit may be based on a digital electrical metering device, it may also have additional functions that include but are not limited to data storage, data transfer, alert signaling, command/control functions, and process control. Detection units may be contacted through "leads", realized as electrodes 160 and 161 (FIG. 1) to one or a plurality of conductive layers. Referring again to FIG. 2, contacts between the conductive layer 295 and detection unit 270 are generally at two positions 265, 267 on the sensing strip. As electrons move in the base member 220, an electromotive force develops between the base member 220 and the conductive layer 295. If the detection unit 270 is a voltmeter device with a very high internal impedance, one can measure the induced emf directly through passive contact of leads 260 and 261 to the conductive layer 295 and the base member 220. The size of the induced effect is proportional to the motional behavior of the induced electrons in the base member 220, while the direction of electron flow in a circuit containing detection unit 270 and electrode leads 260, 261 is such that it generates magnetic fields to opposes the causative fluctuating magnetic fields discussed above (Lenz's Law).

The induced electrical signal is measured across a conductive layer (FIG. 3) or the unit formed by the base member and the conductive layer portion (FIGS. 2 and 6) of a sensor strip in response to the analyte-responsive motions of the charged binding elements in the macromolecule layer 140 (FIG. 1) prior to and during their interaction with analyte. The observed increases in absolute value of a measured electrical signal implies that analyte is present. Baseline readings may be determined from a sample that lacks target analyte or analytes. For example, milk that lacked any antibiotics, gave induced emf readings of 8 millivolts across a base member of aluminum foil and a conductive layer formed by penicillinase and the packaging layer of sodium chloride and glucose. Milk spiked with penicillin at 4.3 parts-per-billion (weight-to-volume) led to a signal of 371 millivolts.

Figure 3:
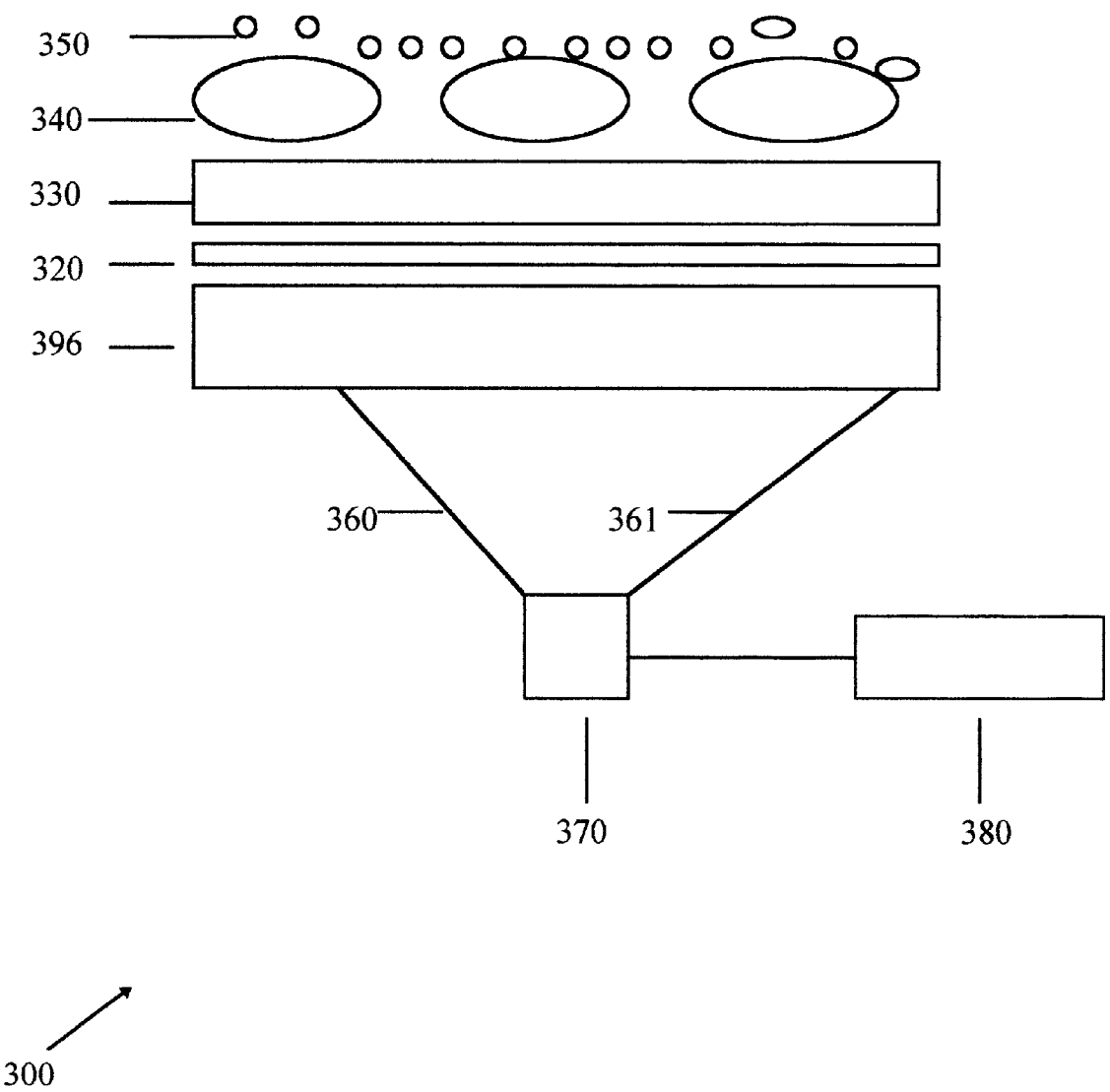
FIG. 3 is a schematic view of a second alternate embodiment of a sensor 300 in accordance with the invention in which a base member 320 with macromolecules 340, SAM 330 and packaging 350 layers are proximate a semiconductor 396, that is contacted by two electrodes 360 and 361 of detection unit 370.

The specific design of a detection unit depends on what quantity (current, magnetic field flux, frequency, impedance, etc.) is being observed. The detection unit may be integrated into a computer 380 as shown in FIG. 3 or other solid-state electronic device for easier signal processing and data storage. The same or a different computer may be used to control sample application in order to monitor both sample source as well as the induced electrical response in the sensor strip conductive layers.

Referring again to FIG. 2, an optional packaging layer 250 for the sensor 200 is a layer of water-soluble chemicals deposited above the immobilized macromolecules 240. The packaging layer 250 is deposited by soaking or spraying methods. The packaging layer 250 serves to stabilize the macromolecules 240 during prolonged storage. In the absence of a packaging layer, oil and dirt may build up on the macromolecules 240 and may interfere with the rapid action of the sensor system. Glucose and a salt, such as sodium chloride, are typically used for the packaging layer 250 so as to guarantee their dissolution in aqueous samples, and thus facilitate direct interaction between macromolecular binding agent (macromolecules 240) and analytes 257. Additionally, for sensor strips that are coated equally on both sides (FIG. 1), the packaging layer also serves as part of the conductive layer, as electrons may pass through charge network formed by the salt ions (FIG. 1). Other hydrophilic chemicals may be chosen for this role, although a deposited conductive layer 295 (FIG. 2) on one side of the sensor strip allows for more consistent electrical contacting with the electrode 260. When the packaging layer (FIG. 1) 150 dissolves, the binding agents are free to immediately interact with analyte 155 and 157 (right side of FIG. 1). Water-soluble polymers, sugars, salts, organic, and inorganic compounds are all appropriate for use in preparation of the packaging layer.

Specifics features of the detection unit such as arrangements of electrodes and modes of response to analyte presence may be found in the co-pending patent applications listed previously.

There are several points to note in regards to the method of detection of analyte as performed by the present invention. Conducting materials are normally at a single electrical potential (voltage) at all points along their surfaces. In the present invention, variations in macromolecular electrostatic fields cause electron motion in a nearby unit comprising conductive base member 620 and semiconducting layer 696 (FIG. 6); motion of these electrons allows for measurement of an induced electrical signal across the unit comprising base member 620 semiconductor 696 by contact of electrodes 660 and 661 from a detection unit 670. The induced electrons do not move as quickly through the semiconductor as they do in the conducting base member, and there is thus an easily measured induced emf as recorded between electrodes 660 and 661. The induced signal in the sensor strip is reflective of induced electron motions in the base member 620. These electrons motions in turn are responsive to the motions of electrostatic fields associated with the macromolecular biding agents and are sensitive to analyte presence, as described previously. The system thus works as a cascade from the action of one or a few binding agents to a recorded signal oftentimes as high as one-half a volt or 10 microamperes across the unit comprising the base-member and the conductive layer portions of the sensor strip.

The implications of the analyte detection methodology are significant. Firstly, detection can take place far away from the point of macromolecule-analyte contact, as the effects of electromagnetically-induced electron motions are propagated throughout the conductive base member. This fact allows for closed-package "food sensing" or the sensing of potentially hazardous samples, e.g. blood, in closed containers. One portion of the sensor contacts the material of interest, while the leads 260 (FIG. 2) of a detection unit 270 are contacted to positions 265 and 267 elsewhere along the sensor strip. This is an important feature of the present sensor. The implications are that any material that can be recognized at a level of specificity by a peptide, protein, antibody, enzyme, nucleic acid single strand, synthetic binding agent, or the like can be detected safely in food, body fluids, air or other samples quickly, cheaply, and with high sensitivity. Response is very rapid. (generally less than 90 seconds in liquid; less that 5 seconds in air), cost is low, and sensitivity has been shown to be very high.

Figure 4:
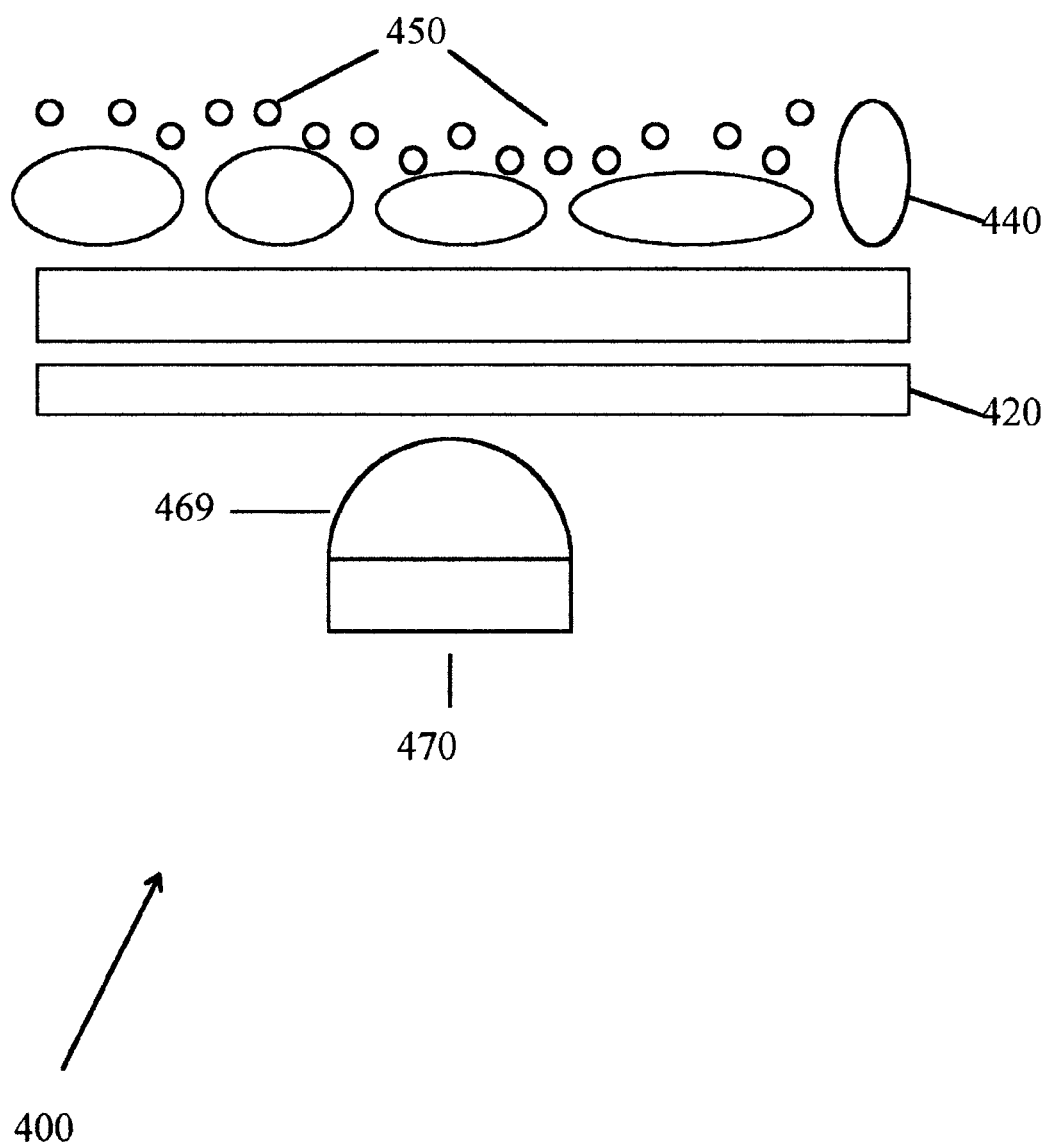
FIG. 4 is a schematic view of a third alternate embodiment of a sensor 400 in accordance with the invention in which fluctuating magnetic fields are measured in a detection unit electrode wire 469 that is placed in proximity to a base member 420, SAM 430, associated macromolecules 440 and packaging layer 450.

An additional point concerns the relationship between the detection unit and the sensor strip. Because the base member produces fluctuating magnetic fields that radiate outwards, one does not need direct contact between the sensor strip and the detection unit. An "electrode wire" is a conductive element that is attached solely to a detection unit. While this element is realized as a wire in the presently preferred embodiment, the conductive element is not restricted to a wire, and the term "electrode wire" is intended to include other types of conductive elements, for example a conductive plate. In FIG. 4, an electrode wire 469 is placed in proximity to the base member 420, but is not in contact with the base member. Fluctuating magnetic fields emanating from the base member may be detected by proximate presence of the electrode wire. In both FIGS. 4 and 5, there is no direct contact between the electrode wire and the sensor strip. In both cases, either air and/or an optional deposited insulating layer (not shown) serves to electrically isolate the electrode wire from the sensor strip. The fluctuations of the binding agent electrostatic material in the presence of analyte cause motion of electrons in a base member. The motion of said electrons causes fluctuating magnetic fields to be generated, and these fields can cause electron motion in a nearby conducting layer as in FIG. 5. The motion of the electrons in the conducting layer (FIG. 5), or from the base member alone as in FIG. 4, can be detected through an appropriate detection unit and associated electrode wire. The resulting increased (in absolute terms) signal is taken to mean that analyte is present. The absence of direct contact between sensor strip and electrodes aids in avoiding spurious signals that might be present.

Figure 5:
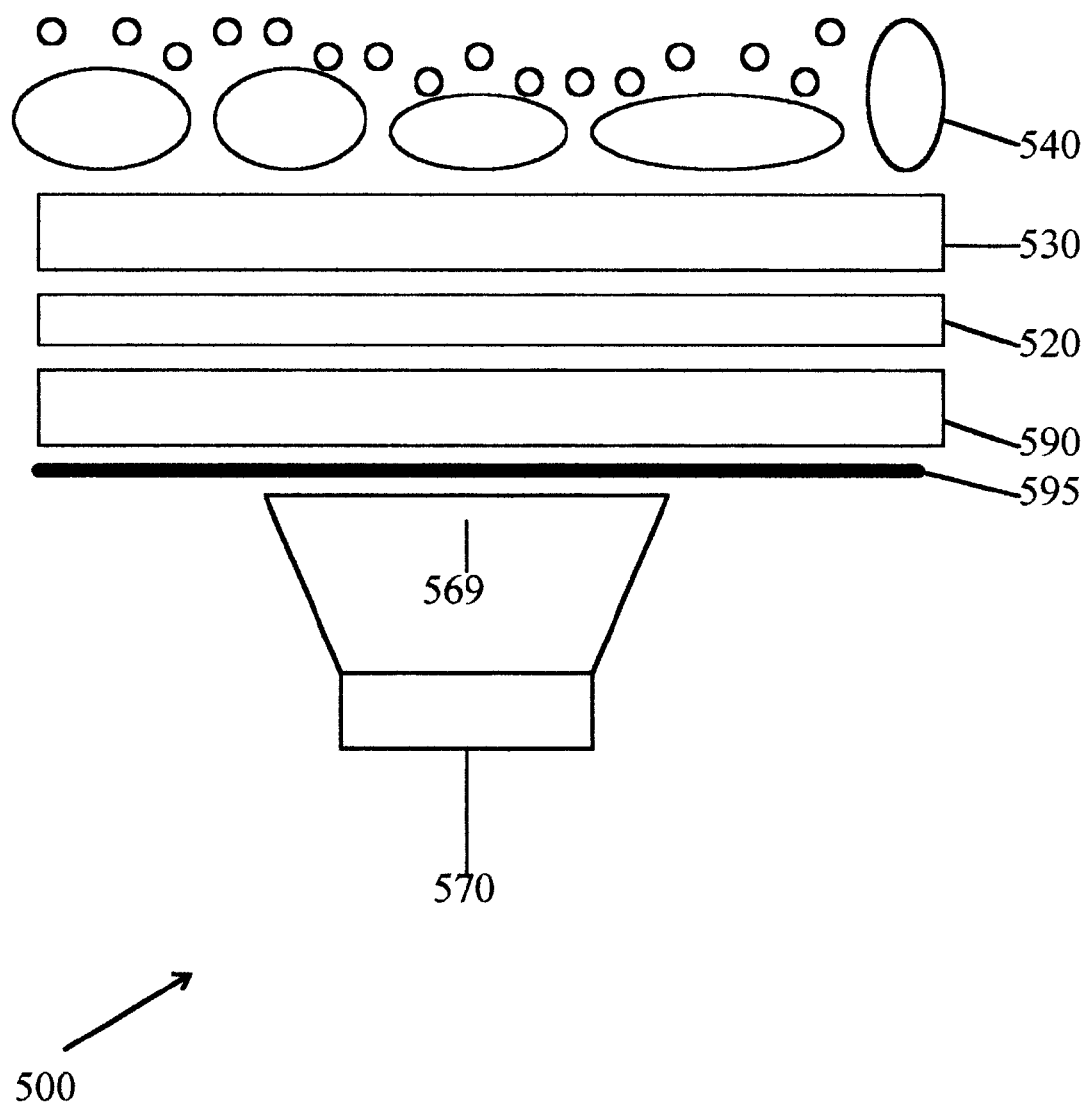
FIG. 5 is a schematic view of a fourth alternate embodiment of a sensor 500 in accordance with the invention in which fluctuating magnetic fields from a conductive layer 595 are measured in an electrode wire 569 of a detection unit 570, the wire being placed in proximity to a chemical layer 590, base member 520, SAM 530, associated macromolecules 540, and packaging layer 550.

The present invention has several advantages:

While the sensor method disclosed in the noted copending applications that are based on induced electrical signals has allowed for rapid determination of analyte presence in complex sample matrices, the issue of electrode contact to sensor strip has heretofore not been fully described. While some embodiments, particularly involving alterations in SAM and addition of a specific conductive layer have allowed for analyte detection, a goal of the present invention is to optimize the specific relationship of sensor strip and detection unit electrodes. Thus, the present invention allows for analyte detection by virtue of induced electron motions in a conductive base member. One may either contact detection unit electrodes to the macromolecule layer 140 and base member 120 (FIG. 1), a specifically applied semiconductive layer 396 (FIG. 3), a semiconductive layer and base member (FIG. 6), base member and a proximate conductive layer (FIG. 2), or there may be no contact between sensor strip and detector electrode whatsoever (FIGS. 4–5). In one embodiment, optimal contact involves one electrode passively contacted to the base member and a second electrode passively contacted to a proximate semiconducting layer as shown in FIG. 6. One may alternatively use direct detection of the fluctuating magnetic fields themselves without recourse to detection of induced electrical signals such as emf and current. The advantage of the present invention is that there is a cascade of moving electronic material, and each cascade leads to larger measurable signal. Thus, the existence of a single binding element-analyte interaction causes the motions of numerous electrons in the conductive portion of the base member. In one embodiment, the motions of these electrons can be detected across a base member-semiconductive layer unit (FIG. 6). It is believed that the action of a few binding agents will cause motions of large numbers of binding agents, due to the change in position of charged moieties of the engaged macromolecules. The motion of large numbers of macromolecules-including those that merely respond to the action of macromolecules interacting with analyte-induces the electron motion in the base member, and said electron motion is the cause of detectable electric or magnetic signals. The base member in the form of a foil may be cut after exposure to sample so as to remove a dry portion of the base member experiencing electron motions and insert it into a detection system.

The following table lists some of the possible components, inducible electrical signals and target application markets relevant to the present invention. Each grouping is independent of the others and one may combine a base member, a macromolecule, and a signal for an application area of choice. The table is in no way meant to be limiting in scope or spirit of the present invention.

| Base Member | Macromolecule | Signal | Application |
| --- | --- | --- | --- |
| Metal | Enzyme | Magnetic Flux | Food Safety |
| Conductive Film* | Antibody | Induced Current | Chemicals |
| Organic Conductor | Nucleic Acids | Impedance | Biologicals |
| Conductive Liquid | Fatty Acid | Resistance | Environment |
| Conductive Ink | Receptor | Sign Switching | Industrial Hygiene |
| Graphite | Synthetic- | Frequency | Internet Medicine |
| Semiconductor | Molecule | Noise Signature | Genetic Testing |
| | Protein | Electromagnetic- | Diagnostics |
| | Peptide | Induction | Process Control |
| | Cell | Capacitance | Drug Screening |
| | Catalytic- | Fourier Transform | Drug Release |
| | Antibody | Band-Pass Filtered | Glucose Testing |
| | Synthetic Receptor | Magnetic Fields | Law Enforcement |
| | Receptor Ligand | | Veterinary- |
| | Antigen | | Testing |

*A conductive film can be deposited on a solid support by any means, including electroless deposition, spin coating, sputtering, vapor deposition, plating, "printing" or dip-coating.

EXAMPLE 1

A 100 millimeter semiconductor-grade n-type silicon wafer is cleaned by oxygen discharge and then sequentially coated with 15 Angstroms of titanium (binder) and 200 nanometers of gold. The coated wafer is immediately placed in an ethanolic solution of 4-mercapto phenol (1 millimolar concentration). The wafer is allowed to soak overnight and then rinsed thoroughly in water. A low advancing water contact angle and low hysteresis suggest excellent binding between the gold and the SAM. The SAM-treated wafer is soaked in lysozyme (5 micrograms/milliliter) in water for 1 hour. The wafer leaves the soak hydrophilic due to the presence of the enzyme. The wafer is immediately soaked in the packaging layer of sodium chloride and glucose. The wafer is allowed to dry and then cut into 1×1 cm$^2$ chips. A silicon side of the chip is contacted with a glued wire (electrode) while a second wire (electrode) is affixed to the gold side of the chip. These electrodes are connected to the positive and negative leads of a digital voltmeter-based detection device. The gold-side of the chip is exposed to liquid samples. The packaging layer readily dissolves in liquid, and the presence of bacteria (analyte) leads to increased voltages as recorded across the gold-semiconducting layers by the detection unit.

EXAMPLE 2

Aluminum foil (Reynolds) is coated on one side with a partially insulating material and then silver paint. On the other side, the foil is coated with a SAM (from stearic acid), binding agents, and packaging layer. Strips are prepared from the foil and used for sensing. The side that contains binding agents is exposed to a sample that may contain analyte. Two electrodes of a detection unit are contacted to the foil base member and to the silver conductive layer (as per the embodiment in FIG. 2). Signals above a predetermined background indicate that the target analyte of interest is present. The detection unit may additionally process, average, smooth, or manipulate raw signal data. It may additionally store information as well as provide alert that analyte is present in the sample.

What is claimed is:

1. A sensor for detecting the presence of an analyte in a sample, comprising:
   (1) one or a plurality of base members, each having an electrically-conductive property;
   (2) at least one macromolecular entity disposed proximate each base member and interactive at a level of specificity with a predetermined analyte, electron motions induced in said base member and responsive to the interaction of said macromolecular entity with analyte;
   (3) a detection unit for detecting said induced electron motions.

2. The sensor according to claim 1, further comprising a conductive layer disposed proximate and electrically-contacted to said conductive base member.

3. The sensor according to claim 2, further comprising chemical layer disposed between said base member and said conductive layer.

4. The sensor according to claim 1, wherein said macromolecular entity comprises a first macromolecular entity capable of interacting at a first specificity and a second macromolecular entity capable of interacting at a second specificity for the detection of at least one analyte.

5. The sensor according to claim 2, wherein electrical leads of said detection unit are coupled to each base member and associated conductive layer at no more than two positions.

6. The sensor according to claim 1, wherein an electrode wire of a detection unit is placed in proximity to each sensor strip.

7. The sensor according to claim 1, wherein each base member is a conducting foil, coating, thin-film, ink, or solid piece.

8. The sensor according to claim 2, wherein said conductive layer has a semiconductive property.

9. The sensor according to claim 2, further comprising a packaging layer disposed above said macromolecular entity, said packaging layer being soluble in the sample medium.

10. The sensor according to claim 1, further comprising a unit to process a signal that is responsive to said induced electron motions.

11. A method for determining presence of an analyte in a sample, comprising the following steps:
    (1) providing one or a plurality of electrically conductive base members;
    (2) immobilizing at least one macromolecule in proximity to each base member, wherein said macromolecule is capable of interacting at a level of specificity with a predetermined analyte;
    (3) exposing sample to at least one base member-macromolecule sensor strip;
    (5) detecting by any means induced motions of electrons in each base member, and said induced electron motions are responsive to analyte presence; and
    (6) comparing a signal caused by said induced electron motions to a known background signal determined in a sample that lacks analyte.

12. The method according to claim 11, further comprising the step of disposing a conductive layer proximate to at least one side of each base member.

13. The method according to claim 11, wherein said macromolecule comprises a first macromolecule capable of interacting at a first specificity and a second macromolecule capable of interacting at a second specificity for the detection of at least one analyte.

14. The method according to claim 12, wherein said step of detecting a signal is performed by contacting electrical leads of a detection unit to the conductive layer and the base member at no more than two positions.

15. The method according to claim 12, wherein an electrode wire is brought into proximity to each conductive layer.

16. The method according to claim 11, wherein each base member is a conducting foil, coating, thin-film, ink, or solid piece.

17. The method according to claim 12, wherein said conductive layer has a semiconductive property.

18. The method according to claim 12, further comprising the step of disposing a packaging layer above said macromolecules, said packaging layer being soluble in the sample medium.

19. The method according to claim 11, further comprising the step of processing said signal or a component thereof.

20. The method in accordance with claim 11, further comprising the steps of:
    removing a portion of said sensor strip; and
    submitting said removed portion to a detection system for analysis thereof.

* * * * *